(12) United States Patent
Tyber et al.

(10) Patent No.: US 8,414,651 B2
(45) Date of Patent: Apr. 9, 2013

(54) DYNAMIC INTERBODY

(75) Inventors: Jeffrey Tyber, Bethlehem, PA (US);
Jeffrey Kozak, Houston, TX (US);
Robert Narotzky, Casper, WY (US)

(73) Assignee: Aesculap Implant Systems, LLC, Center Valley, PA (US)

( * ) Notice: Subject to any disclaimer, the term of this patent is extended or adjusted under 35 U.S.C. 154(b) by 1445 days.

(21) Appl. No.: 12/015,276

(22) Filed: Jan. 16, 2008

(65) Prior Publication Data
US 2009/0182430 A1 Jul. 16, 2009

(51) Int. Cl.
*A61F 2/44* (2006.01)
(52) U.S. Cl.
USPC ....................................... 623/17.15
(58) Field of Classification Search ............... 623/17.15, 623/17.16; 606/71
See application file for complete search history.

(56) References Cited

U.S. PATENT DOCUMENTS

| | | | |
|---|---|---|---|
| 4,904,261 A | 2/1990 | Dove et al. | |
| 5,443,515 A * | 8/1995 | Cohen et al. | 623/17.16 |
| 5,458,641 A * | 10/1995 | Ramirez Jimenez | 623/17.11 |
| 6,214,005 B1 * | 4/2001 | Benzel et al. | 606/250 |
| 6,395,030 B1 * | 5/2002 | Songer et al. | 623/17.11 |
| 6,432,106 B1 * | 8/2002 | Fraser | 623/17.11 |
| 6,660,038 B2 | 12/2003 | Boyer | |
| 6,984,234 B2 | 1/2006 | Bray | |
| 7,041,135 B2 | 5/2006 | Michelson | |
| 7,077,864 B2 | 7/2006 | Byrd et al. | |
| 7,112,222 B2 | 9/2006 | Fraser et al. | |
| 7,232,464 B2 | 6/2007 | Mathieu et al. | |
| 2003/0229348 A1 * | 12/2003 | Sevrain | 606/70 |
| 2004/0127991 A1 * | 7/2004 | Ferree | 623/17.11 |
| 2004/0254644 A1 | 12/2004 | Taylor | |
| 2005/0177236 A1 * | 8/2005 | Mathieu et al. | 623/17.11 |
| 2006/0085071 A1 * | 4/2006 | Lechmann et al. | 623/17.11 |
| 2006/0293749 A1 * | 12/2006 | Hudgins et al. | 623/17.11 |
| 2007/0093901 A1 | 4/2007 | Grotz | |
| 2008/0177263 A1 * | 7/2008 | Freedman et al. | 606/71 |
| 2009/0210064 A1 | 8/2009 | Lechmann et al. | |

FOREIGN PATENT DOCUMENTS

| | | |
|---|---|---|
| WO | WO2004/069106 | 7/2005 |
| WO | WO2006/040063 | 4/2006 |

OTHER PUBLICATIONS

Non-Final Office Action Dated Feb. 16, 2011, for U.S. Appl. No. 12/256,713.
Office Action for U.S. Appl. No. 12/019,760, mailed Jun. 8, 2011.
Non-Final Office Action Dated May 11, 2011, for U.S. Appl. No. 12/256,713.
Final Office Action for U.S. Appl. No. 12/414,103, Mailed Jul. 17, 2012, 19 pgs.

* cited by examiner

*Primary Examiner* — Kevin T Truong
*Assistant Examiner* — David Bates
(74) *Attorney, Agent, or Firm* — RatnerPrestia

(57) ABSTRACT

An intervertebral implant includes a body having an upper surface, a lower surface and a transverse fastener hole. The body includes a dynamic fixation mechanism for seating a fastener in the fastener hole and translating the fastener relative to the implant to accommodate subsidence of the implant. In one embodiment, an implant includes a transverse slot with an elongated seat for translating a seated fastener relative to the implant. In another embodiment, an implant includes a displaceable sliding member for translating a fastener relative to the implant.

17 Claims, 14 Drawing Sheets

DYNAMIC INTERBODY

FIELD OF THE INVENTION

The present invention relates generally relates to intervertebral implants, and more specifically to interbody components with mechanisms for dynamically transmitting loads during interbody subsidence.

BACKGROUND OF THE INVENTION

Anterior lumbar interbody fusion (ALIF) is a common technique for treating degenerative discs from an anterior approach. The anterior approach allows access to the interbody space with minimal damage to the posterior musculature, while allowing full decompression of the diseased disc. The ALIF procedure has been used with lumbar plates and cages with screws rigidly affixed within the construct. A number of cages include an interbody with a hollow or open area in the center which receives bone graft material. The bone graft material fuses the adjacent vertebrae is together.

SUMMARY OF THE INVENTION

In accordance with one exemplary embodiment of the invention, an intervertebral implant includes an upper surface generally conforming to a plane and a lower surface generally conforming to a plane. A fastener hole having a longitudinal axis extends transversely through one of the plane of the upper surface and the plane of the lower surface. The implant further includes means for seating a fastener in the fastener hole and translating the seated fastener within the fastener hole.

In another exemplary embodiment of the invention, an intervertebral implant includes an upper surface generally conforming to a plane, a lower surface generally conforming to a plane, a slot having a longitudinal axis extending transversely through one of the plane of the upper surface and the plane of the lower surface, and an elongated seat at an end of the slot for translating a seated fastener head within the slot.

In another exemplary embodiment of the invention, an intervertebral implant includes an upper surface for at least partial engagement with an end plate of a first vertebrae, the upper surface generally conforming to a plane, and a lower surface for at least partial engagement with an end plate of a second vertebrae, the lower surface generally conforming to a plane. A first fastener hole has a longitudinal axis extending transversely through the plane of the upper surface, and an elongated cross section. A second fastener hole has a longitudinal axis extending transversely through the plane of the lower surface, and an elongated cross section.

In another exemplary embodiment of the invention, an intervertebral implant includes an upper surface and a lower surface, and a sliding member displaceable in a plane passing through the upper surface and the lower surface. A fastener slot extends through the sliding member, the slot having a longitudinal axis extending transversely through one of the upper surface and the lower surface.

In another exemplary embodiment of the invention, an intervertebral implant includes an upper surface for at least partial engagement with an end plate of a first vertebrae, and a lower surface for at least partial engagement with an end plate of a second vertebrae. The implant further includes an anterior surface extending between the upper surface and the lower surface, and a cover detachably connected over the anterior surface. The cover may include an exterior surface following a convex curvature. In addition, or as an alternative, the cover may be coated with a bioactive surface. The anterior surface of the implant may include a plurality of fastener holes and a plurality of screw fasteners extending through the fastener holes, with the cover forming a fixture on the implant preventing displacement of the screws out of the fastener holes.

BRIEF DESCRIPTION OF THE DRAWINGS

The foregoing summary and the following description will be more clearly understood in conjunction with the drawing figures, of which.

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

The fusion interbody assembly of the present invention improves upon prior approaches by addressing, among other issues, the occurrence of subsidence and settling of the implant into the surrounding vertebrae. Applicants have discovered a number of problems and drawbacks associated with interbody cages that use rigidly constrained fixation members, such as bone screws that are fixed in angulation and position relative to the interbody. Interbody cages are capable of subsiding into endplates of adjacent vertebra by as much as 6 mm. When fixation screws are rigidly constrained in the interbody, the fixation screws provide resistance against subsidence, absorbing much of the load during settling. This creates a number of concerns. First, the screws are not optimal for receiving loads caused by settlement, and may be compromised if these loads are excessive. Second, because the fixation screws absorb the loads that occur from subsidence, the fixation screws and interbody provide stress shielding to the bone graft material. Wolff's Law recognizes that bone material is a living structure that adapts to loads and remodels itself over time to accommodate the loads. Bone material grows and becomes stronger in response to increased stresses. If bone graft material is shielded from loads that occur during settlement, bone growth will be inhibited and fusion will not occur properly. Subsidence has been linked to pseudoarthrodesis and non-union of the fusion site.

The various embodiments of the present invention allow proper load distribution to the bone graft material during subsidence, while still utilizing fixation members like bone screws within the disc space. This is accomplished by allowing fixation to occur over time as a dynamic process in response to subsidence and settling. Rather than absorb loads that occur during subsidence, the bone screws are permitted to translate and/or pivot with respect to the interbody as the implant subsides. This allows the subsidence loads to be transferred to the bone graft material, rather than be absorbed by the bone screws. To accomplish this, the embodiments include translation mechanisms that allow the fixation members to translate and pivot in response to subsidence and settlement, while maintaining the fixation members firmly anchored in the implant. The translation mechanism may take a number of forms, as will be appreciated from the exemplary embodiments described in the following sections.

Figure 1:
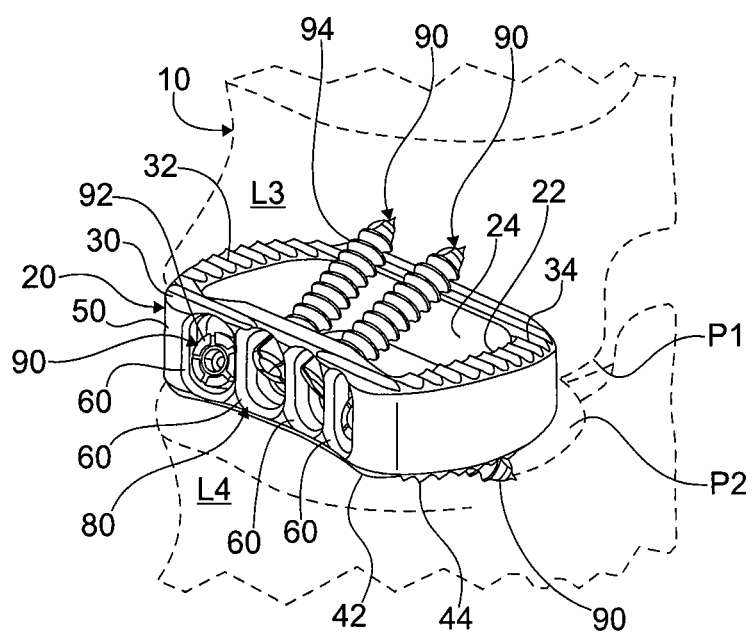
FIG. 1 is a perspective view of an exemplary implant in accordance with one embodiment of the invention, schematically showing the implant positioned between two vertebral bodies.
Figure 2:
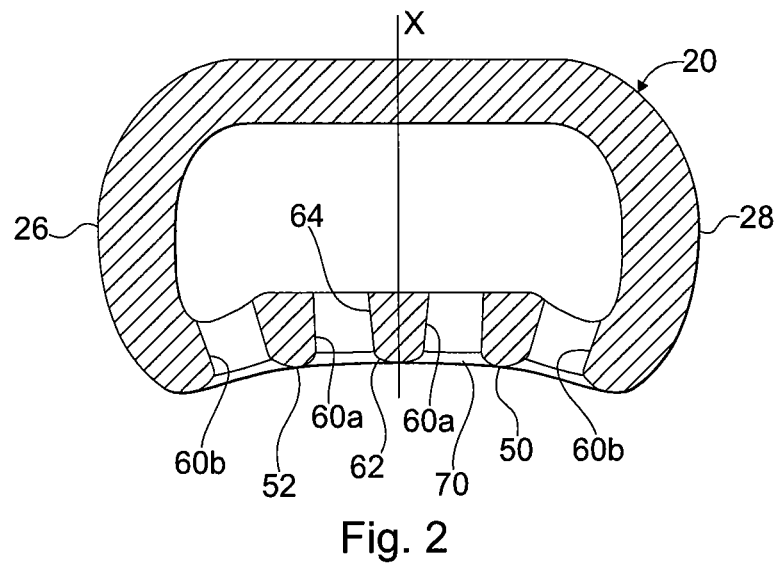
FIG. 2 is a top cross-sectional view of a component shown in FIG. 1.
Figure 3:
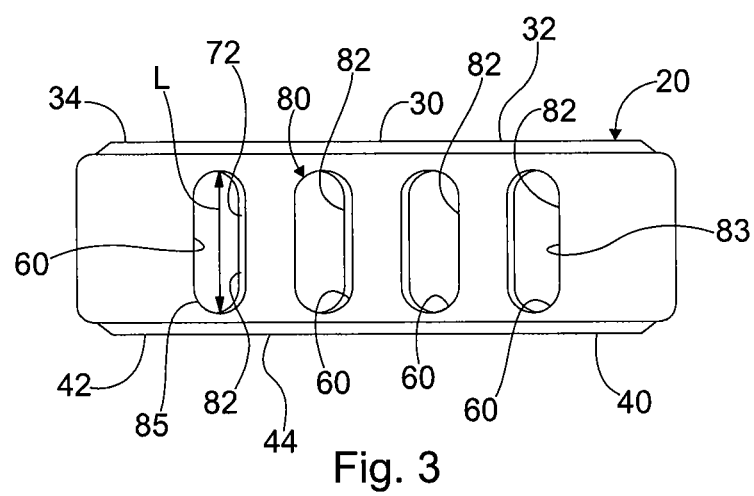
FIG. 3 is a front view of a component shown in FIG. 1.

Referring now to FIGS. 1-3, an exemplary intervertebral implant 10 in accordance with one embodiment of the invention is shown. Implant 10 includes a generally ring-shaped body 20 inserted between two vertebrae for fusion of the vertebrae. Body 20 forms a hollow interior 22 that provides a bone graft space 24. A plurality of bone fixation members 90 are used to secure implant 10 in the disc space. Bone fixation members 90 cooperate with other components of implant 10 to provide a dynamically controlled fixation that accommodates subsidence of the implant while maintaining the rigidity of connection between the fixation members, the body and the vertebrae.

Implants in accordance with the present invention may be secured using a number of different screw configurations, or other types of anchors. Because subsidence of the implant can cause some anchors to loosen or "back out" of their holes in the vertebrae, the implants of the present invention preferably include anchors having a locking mechanism that locks a portion of the anchor to the implant, while still permitting translation and pivoting during subsidence. For example, a bone screw with a head that locks into a receiving part may be used, such as that shown in International Pub. No. WO 2006/040063 A1 to Peukert, et al., the contents of which is incorporated by reference herein. The Peukert screw features a slotted head with a mechanism for expanding the head outwardly. Expansion of the screw head forms a compression fit with the receiving slot to protect against screw back out.

The implants in accordance with the present invention may be used in various areas of the spine, including areas in the cervical, thoracic and lumbar regions of the spine. Implant 10 is schematically shown implanted between two lumbar vertebrae, L3 and L4. This location is shown for illustrative purposes only, and implants in accordance with the invention may be used between other vertebrae. An upper surface 30 engages a superior end plate P1 on vertebra L3, and a lower surface 40 engages an inferior end plate P2 on vertebra L4. For purposes of this description, the term "upper" will refer to features that face or extend toward a superior vertebra in the implanted state, the term "lower" will refer to features that face or extend toward an inferior vertebra in the implanted state, the term "anterior" will refer to features that face or extend toward the anterior side of the spine in the implanted state, and the term "posterior" will refer to features that face or extend toward the posterior side of the spine in the implanted state.

Figure 16:
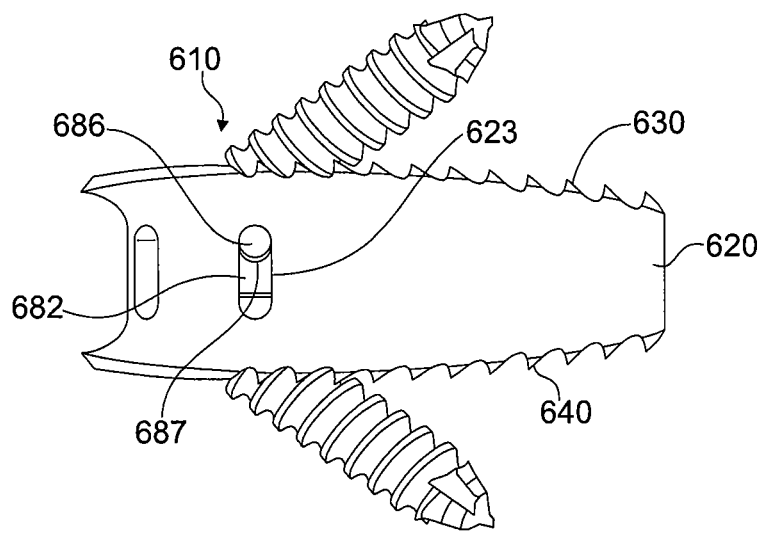
FIG. 16 is a schematic side view of the implant of FIG. 14 in the first setting.
Figure 17:
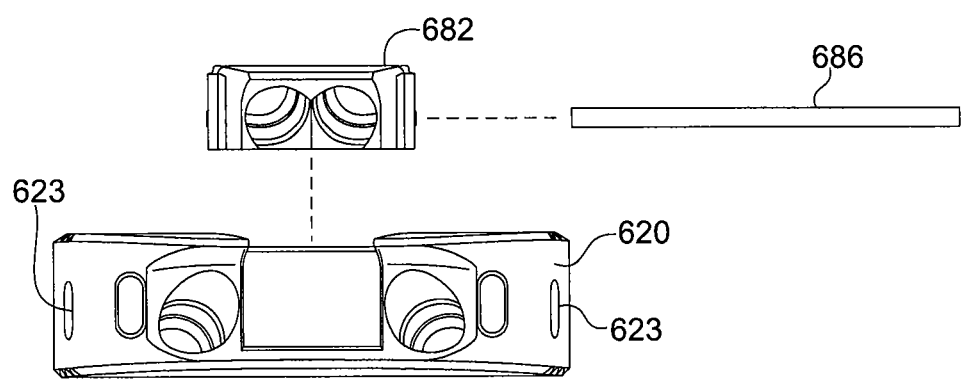
FIG. 17 is an exploded view of components of the implant of FIG. 14.

Upper and lower surfaces 30, 40 are generally planar. It will be noted that the generally planar upper and lower surfaces may feature a small curvature, 25 such as a slight convex curvature as shown with surfaces 630, 640 in FIG. 16, or be more or less flat. Regardless of the general shape of the upper and lower surfaces, implants of the present invention preferably include textured or irregular surfaces to enhance ingrowth of adjacent bone. In FIG. 1, for example, upper surface 30 includes an engagement surface 32 with a plurality of sharp ridges 34. Similarly, lower surface 30 40 includes an engagement surface 42 with a plurality of sharp ridges 44. The ridges 34, 44 are configured to engage their respective end plates and provide a firm connection that resists slippage or shifting of the implant in the anterior-posterior plane.

An anterior surface 50 extends between upper and lower surfaces 30, 40. A plurality of fastener holes 60 extend through body 20 on the anterior side, and penetrate through anterior surface 50. Each fastener hole 60 is adapted to receive an elongated fixation member that anchors the body 20 in the intervertebral space. A number of fastener hole configurations may be used in accordance with the present invention, as will be appreciated from the embodiments to be described. Body 20 includes a pair of inner fastener holes 60a and a pair of outer fastener holes 60b. Inner and outer fastener holes 60a, 60b each have a longitudinal axis (i.e. axis extending in the direction of penetration through body 20) that is sloping or transverse relative to the upper and lower surfaces 30, 40.

Each inner hole 60a has a longitudinal axis that intersects the plane of upper surface 30. In this arrangement, inner holes 60a extend toward a superior vertebra in the implanted state. Conversely, each outer hole 60b has a longitudinal axis that intersects the plane of lower surface 40. In this arrangement, outer holes 60b extend toward an inferior vertebra in the implanted state. Fastener holes 60 are also angled laterally with respect to the implant, as shown in FIG. 2. Two of the holes 60 extend toward a left side 26 of body 20, and two of the holes extend toward a right side 28 of body 20. Fastener holes 60 are preferably oriented in a symmetrical arrangement with respect to at least one axis of the implant. In FIG. 2, for example, fastener holes 60 are symmetrically arranged with respect to anterior-posterior axis "X." Inner fastener holes 60a have a diverging axis of entry with respect to axis X, and outer fastener holes 60b have a diverging axis of entry with respect to axis X. A symmetrical arrangement of the fastener holes, and consequently the fixation members, provides a more balanced resistance to stress forces, and a more uniform hold.

Referring again to FIG. 1, fastener holes 60 each contain a fixation screw 90. Each screw 90 includes a rounded locking head 92 similar to those described in International Pub. No. WO 2006/040063 A1 and a threaded shank 94. Screws 90 that are inserted through inner fastener holes 60a extend through the bone graft space 24 and the plane of upper surface 30. Screws 90 that are inserted through inner fastener holes 60b extend through the bone graft space 24 and the plane of lower surface 40. Because screws 90 are able to translate and pivot in response to subsidence, loads applied to body 20 and screws 90 are distributed into the graft space.

The anterior surface and/or fastener holes may be arranged so as to minimize the risk of adverse interaction with blood vessels and other parts of the anatomy on the anterior side of the spine. Anterior surface 50 has a generally concave curvature 52 that bows inwardly toward the center of body 20. This arrangement reduces the potential for screw heads contacting blood vessels outside the disc space on the anterior side of the spine.

As discussed above, implant 10 includes a translation mechanism 80 that allows screws 90 to adjust in response to subsidence and settling of the implant. Translation is provided in particular by slotted openings 82 that coincide with fastener holes 60, and the cross-sectional configurations of the fastener holes. Each slotted opening 82 is formed with straight sides 83 and rounded ends 85. Straight sides 83 extend generally perpendicularly to the planes of upper and lower surfaces 30, 40, forming elongated openings with long dimensions extending more or less parallel to the length of the spine. The dimensions of slotted openings 82 are larger than the maximum expanded diameters of screw heads 92, thus being adapted to receive screws 90 and allow screw heads 92 to pass through the slotted openings. Each fastener hole 60 has a widened cross section 62 in proximity to its respective slotted opening 82. The cross-section of fastener hole transitions from widened cross section 62 to a reduced cross-section 64. The transition between widened cross section 62 and reduced cross section 64 forms a rounded seat 70. The cross-sectional dimensions of widened section 62 are larger than the diameters of screw heads 92, while the cross-sectional dimensions of reduced section 64 are smaller than the diameters of the screw heads. Both sections 62 and 64 have cross-sectional dimensions that are larger than the maximum dimensions of screw shanks 94. In this arrangement, each fastener hole 60 allows insertion of screw shank 94 through the anterior wall of body 20, with seat 70 preventing screw head 92 from passing completely into reduced section 65.

Seat 70 generally follows the shape of slotted opening 82, with elongated sides and rounded ends forming a track 72. Track 72 provides a surface on which screw heads 92 can be slidably displaced when screws 90 are inserted in fastener holes 60. The elongated shape of each track 72 allows a limited range of linear translation of a screw head relative to body 20. The range of linear translation is represented in FIG. 3 by arrows "L". Seats 70 also permit a limited range of pivoting of screws 90 and screw heads 92 with respect to anterior surface 50. This can be visualized from the schematic illustration in FIG. 1.

Translation and pivoting of screws 90 is also facilitated by the cross sectional shapes of fastener holes 60. Rather than having cylindrical bores, fastener holes 60 have elongated cross sectional shapes that allow the shank to both translate and/or pivot with respect to the anterior surface of body 20. The dimensions of fastener holes preferably limit the amount of translation and pivoting to ranges that correspond to an expected amount of subsidence and settling.

The dimensions of the implant of the present invention may vary, depending on factors including the particular region of the spine and other parameters. For example, an implant body to be used in the lumbar region may be larger than an implanted body to be used in the cervical region. Implants having a total height of about 11 mm and fixation placement within about 17.5 mm of the midline are suitable for purposes of the invention, although implants with larger or small sizes and different placements may also be satisfactory.

Figure 4:
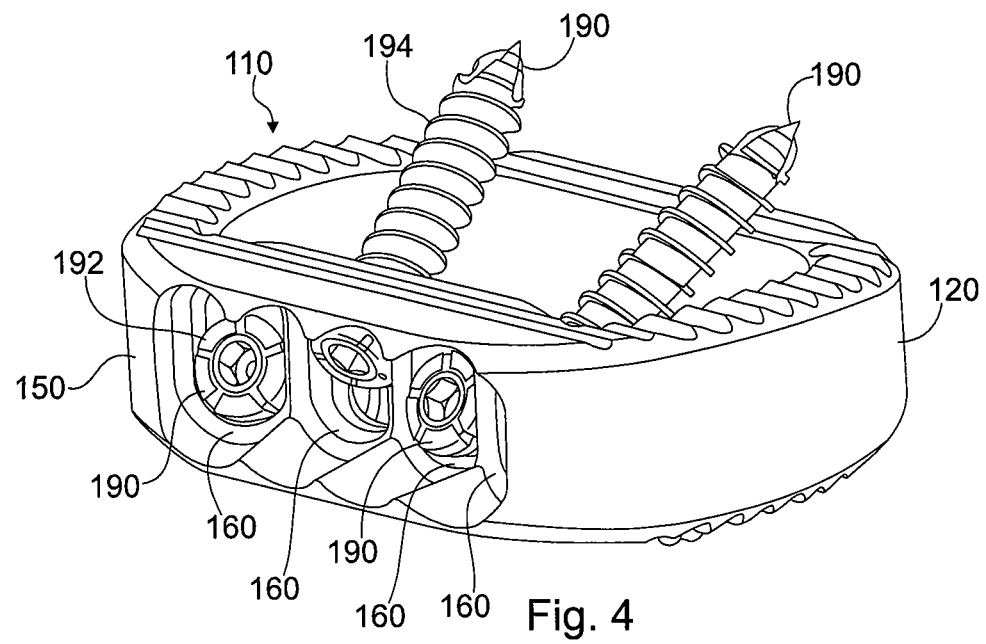
FIG. 4 is a perspective view of an exemplary implant in accordance with another embodiment of the invention.

Referring now to FIG. 4, an exemplary implant 110 in accordance with another embodiment of the invention is shown. Implant 110 has a ring-shaped body 120 that features a substantially flat anterior surface 150. The flat anterior surface forms a wider anterior wall on body 120. The wider anterior wall forms a relatively deep recess within which a plurality of bone screws 190 are inserted into fastener holes 160. The screw heads 192 on bone screws 190 are recessed inside the anterior surface, and are thus positioned further within the perimeter of the interbody as compared to implant 10.

Figure 5:
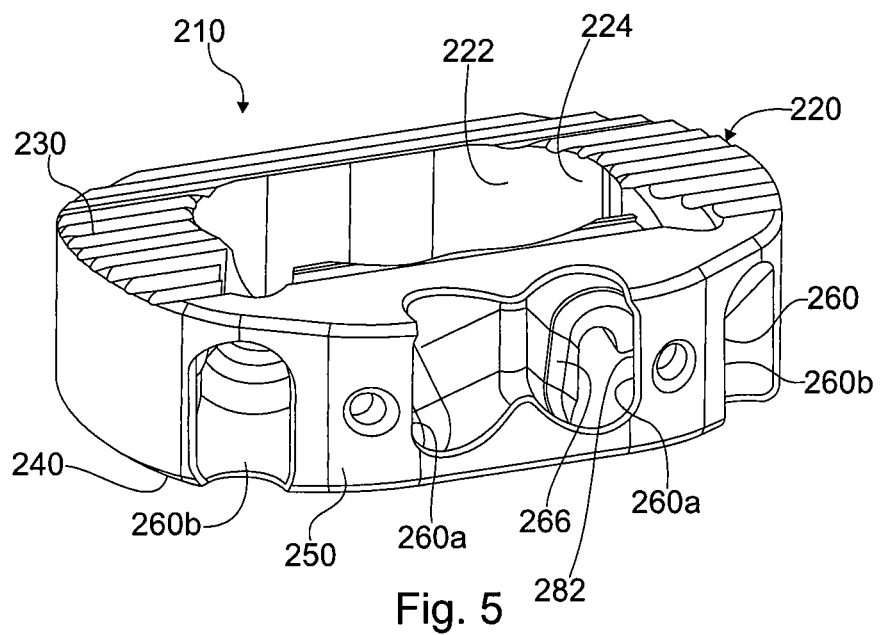
FIG. 5 is a perspective view of an exemplary component in accordance with another embodiment of the invention.
Figure 6:
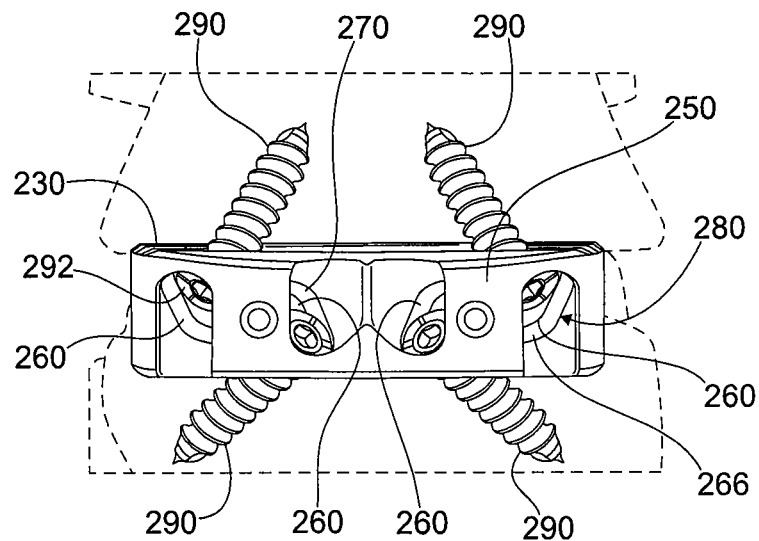
FIG. 6 is a front view of the component of FIG. 5, schematically showing the component implanted between two vertebral bodies in a first setting.
Figure 7:
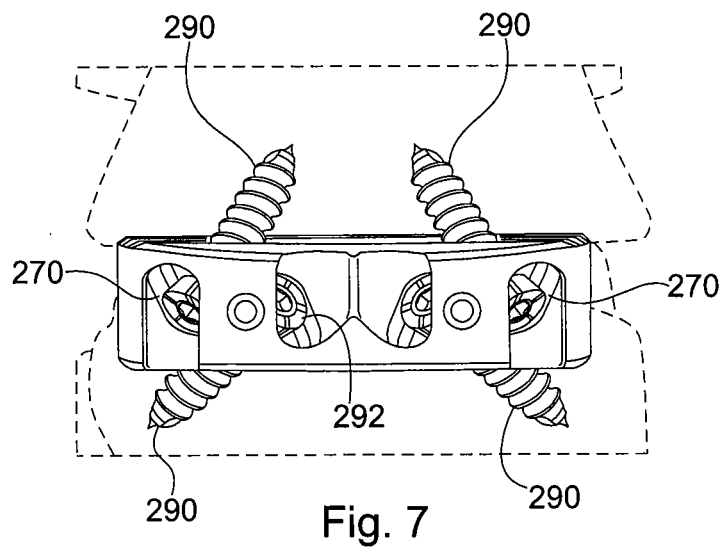
FIG. 7 is a front view of the component of FIG. 5, schematically showing the component implanted between two vertebral bodies in a second setting.

Referring now to FIGS. 5-7, an exemplary implant 210 in accordance with another embodiment of the invention is shown. Implant 210 includes a generally ring-shaped body 220 that forms a hollow interior 222. Hollow interior 222 provides a space 224 for bone graft material. Body 220 includes an upper surface 230, a lower surface 240 and an anterior surface 250. A plurality of fastener holes 260 extend through body 220 on the anterior side, and penetrate through anterior surface 250. Fastener holes 260 are configured to gradually increase the amount of resistance to subsidence, while still maintaining the ability to dynamically translate as greater loads are applied. A pair of diverging inner holes 260a extend outwardly and downwardly from anterior surface 250 toward the plane of lower surface 240. A pair of converging outer holes 260b extend inwardly and upwardly from anterior surface 250 toward the plane of upper surface 230. Each of the inner holes 260a and outer holes 260b aligns with an elongated slot opening 282.

Fastener holes 260 cooperate with bone screws 290 to form a dynamic fixation. Each fastener hole 260 contains a seat 270 for engaging a screw head 292 on a bone screw 290. In addition, each fastener hole 260 includes an elongated cross-section 266. The seat 270 and elongated cross-section 266 provide a translation mechanism 280 that allows subsidence loads to be distributed to the graft area in a controlled manner. FIGS. 6 and 7 schematically illustrate the dynamic translation of bone screws 290 during subsidence in one possible scenario. It is noted that for implant 210, and all implants illustrated herein, the illustrated screw translations are exemplary. The actual orientation of the screws after translation may appear in a number of arrangements, including but not limited to arrangements where some screws translate more than others. FIG. 6 illustrates the relative position of the screws before subsidence of the implant into the adjacent end plates. FIG. 7 illustrates the relative position of the screws after subsidence of the implant into the adjacent end plates is complete. Each screw head 292 undergoes a unidirectional translation. Because the seats 270 are oriented at oblique angles with respect to the anterior face, the force required to translate the screw heads 292 relative to the seats gradually increases so that greater and greater resistance to translation is applied during subsidence. The slanted orientations of seats 270 also gradually increase the holding strength of the implant as subsidence occurs. A variety of angular orientations may be used with satisfactory results. In implant 210, fastener holes 260 are oriented so that screws enter the implanted body 220 at an angle of 40 degrees relative to the cranial-caudal axis and 30 degrees relative to the medial-lateral axis.

Figure 8:
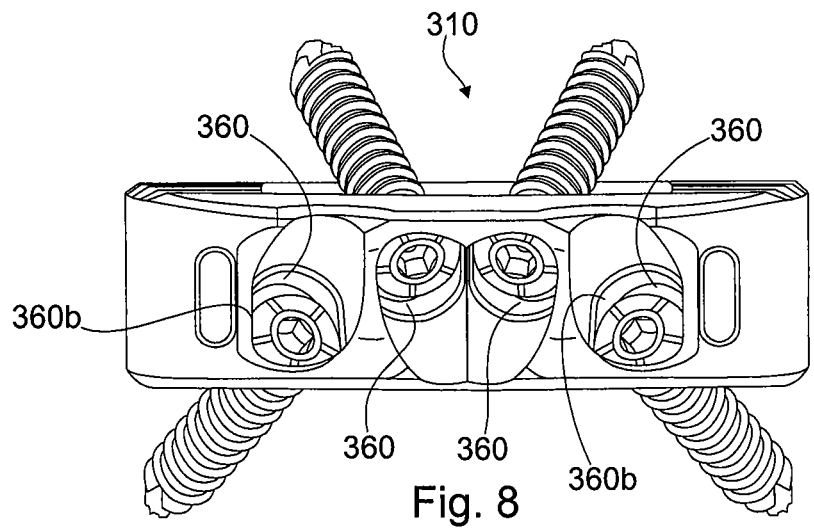
FIG. 8 is a front view of an exemplary implant in accordance with another embodiment of the invention.

Referring now to FIG. 8, an exemplary implant 310 in accordance with another embodiment of the invention is shown. Implant 310 is similar in some respects to implant 210, but includes fastener holes 360 having different axes of entry than those of implant 210. Among other differences, implant 310 includes outer fastener holes 360b that diverge from one another outwardly, rather than converge inwardly.

Figure 9:
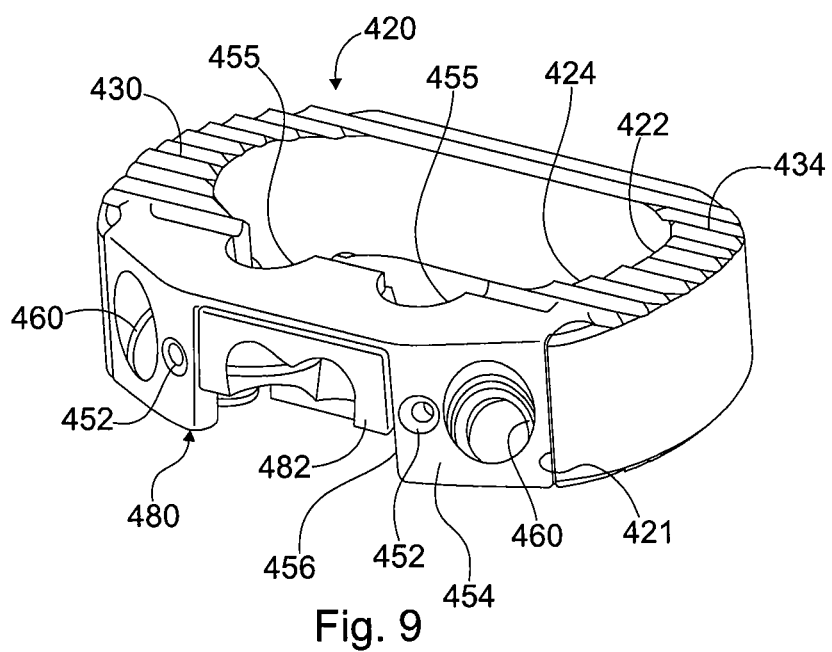
FIG. 9 is a perspective view of an exemplary component in accordance with another embodiment of the invention.
Figure 10:
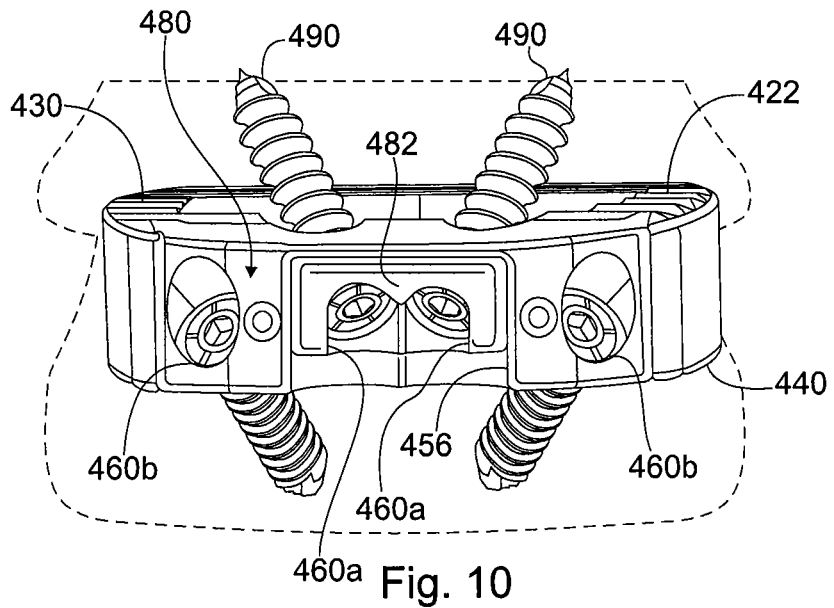
FIG. 10 is a front view of the component of FIG. 9, schematically showing the component implanted between two vertebral bodies in a first setting.
Figure 11:
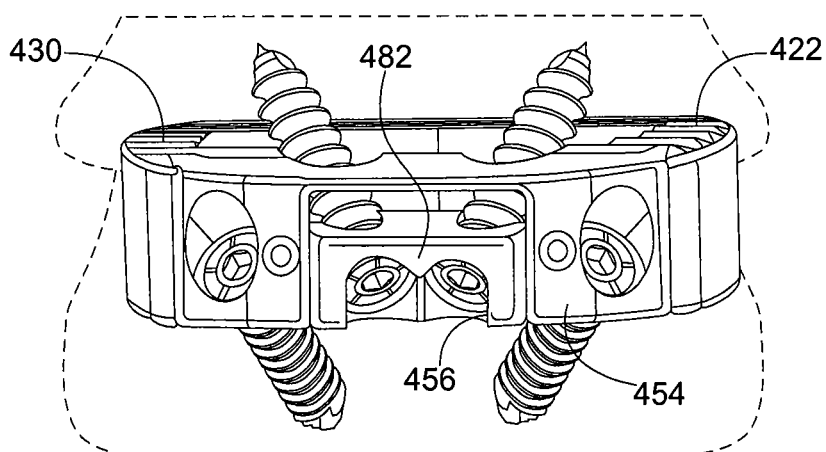
FIG. 11 is a front view of the component of FIG. 9, schematically showing the component implanted between two vertebral bodies in a second setting.

Referring now to FIGS. 9-11, an exemplary implant 410 in accordance with another embodiment of the invention is shown. Implant 410 features an interbody 420 with a large anterior recess 421. Recess 421 houses a translation mechanism 480 that includes an outer plate 454 and an inner plate 482. Outer plate 454 forms a pocket 456 in which inner plate 482 is mounted. Inner plate 482 is slidable in pocket 456 relative to outer plate 454. Two sets of generally cylindrical fastener holes 460 extend through inner plate 482 and outer plate 454. A pair of inner fastener holes 460a extend through inner plate 482 with axes that diverge outwardly. A pair of outer fastener holes 460b extend through outer plate 454 and converge inwardly. Outer plate 454 may include engagement surfaces that conform to engagement surfaces on interbody 420. For example, outer plate 454 may include a plurality of ridges that conform to ridges 434 on an upper surface 430 of interbody 420. Outer plate 454 may also include a pair of circular notches or cutouts 455, as shown in FIG. 9, that permit a portion of the bone screws or other fixation components to pass upwardly through part of the outer plate and into graft space 424.

Inner plate 482 and outer plate 454 are displaceable and operable independently in response to subsidence of the implant in the superior end plate and/or inferior end plate. In particular, inner plate 482 is slidable in pocket 456 so as to move relative to outer plate 454 and interbody 420. Outer plate 454 is slidable in recess 421 so as to move with respect to interbody 420. Pocket 456 and recess 421 can be arranged to limit the amount of relative displacement of the inner and outer plates 482, 454. For example, pocket 456 may be configured so as to allow a displacement of inner plate 482 by as much as 3 mm during subsidence. Recess 421 may be configured so as to allow a displacement of outer plate 454 by up to 1.5 mm. More or less displacement may be permitted, depending on the anticipated amount of settling, the dimensions of components or other parameters. Outer plate 454 includes a pair of engagement holes 452 that cooperatively engage an instrument, such as a guiding device, holder, retractor system or other tool for manipulating implant 410.

FIGS. 10 and 11 schematically illustrate the dynamic translation of a plurality of bone screws 490 during subsidence of implant 410 in one possible scenario. In particular, FIG. 10 illustrates the relative position of bone screws 490 before subsidence of implant 410 into the adjacent end plates. FIG. 11 illustrates the relative position of bone screws 490 after subsidence of implant 410 into the adjacent end plates. Prior to subsidence, inner plate 482 is positioned toward an upper surface 430 of implant 410. After subsidence, inner plate 482 is positioned toward a lower surface 440 of implant 410.

Figure 12:
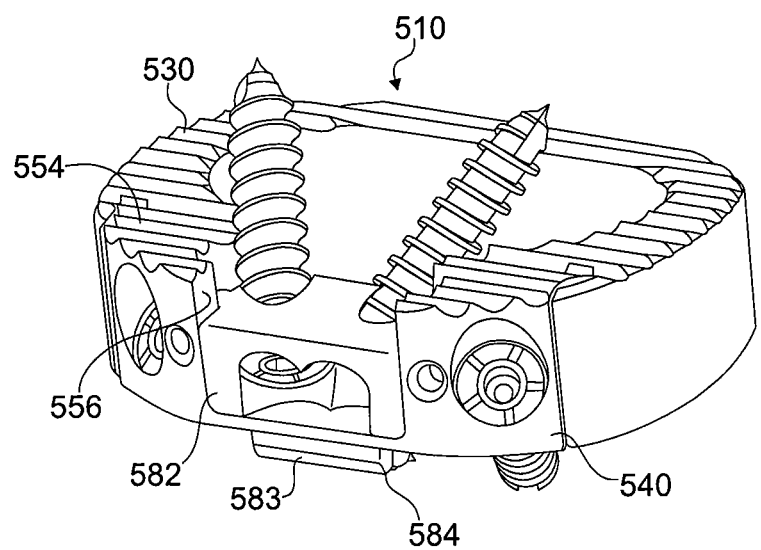
FIG. 12 is a perspective view of an exemplary implant in accordance with another embodiment of the invention.
Figure 13:
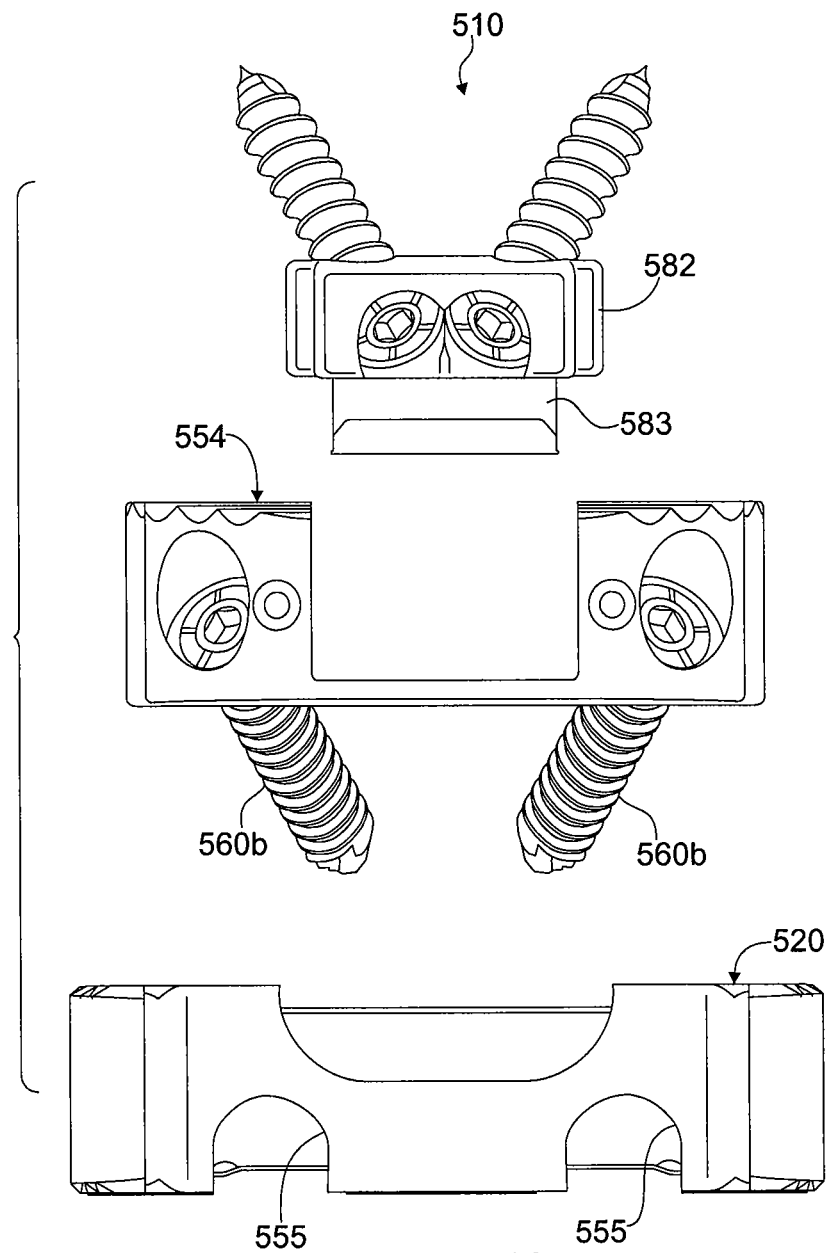
FIG. 13 is an exploded view of the implant of FIG. 12, with some of the components separated from one another.

In some circumstances, it may be desirable to provide one or more mechanisms for additional stability after subsidence. Referring now to FIGS. 12 and 13, an exemplary implant 510 in accordance with another embodiment of the invention is shown. Implant 510 is similar to implant 410 discussed above, but includes a fixation extension 583 for increased stability. A pocket 556 opens toward an upper surface 530 of the implant, and contains an inner plate 582. Inner plate 582 is displaceable in pocket 556 to permit translation of bone screws during subsidence of implant 510. FIG. 12 shows inner plate 582 in a position corresponding to how it would appear after implant 510 undergoes subsidence in one possible scenario. Inner plate 582 is displaced toward a lower surface 540 of implant 510. Fixation extension 583 projects through the bottom of outer plate 554 and below lower surface 540. The bottom portion of fixation extension 583 includes a sharp edge 584. Sharp edge 584 is configured to penetrate into the inferior end plate during subsidence, providing additional stability of implant 510 and resistance to movement between the vertebrae.

FIG. 13 shows components of implant 510 separated from one another. Body 520 includes a pair of cutouts 555 that permit outer bone screws 560b to pass upwardly through the outer plate and into a graft space in the interior of body 520.

Figure 14:
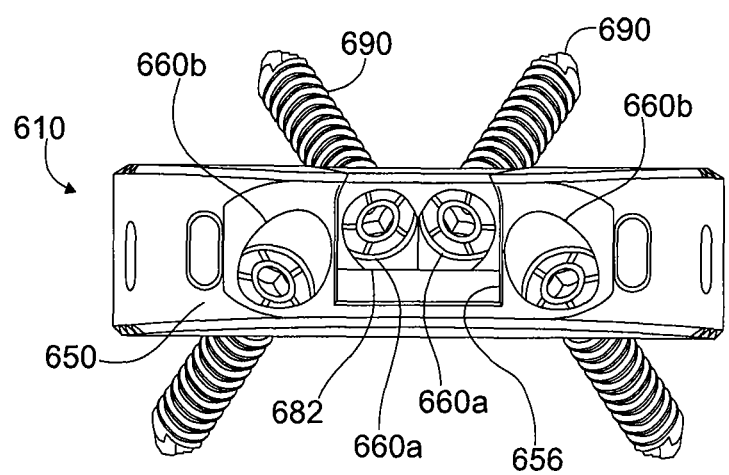
FIG. 14 is a front view of an exemplary implant in accordance with another embodiment of the invention, showing the implant in a first setting.
Figure 15:
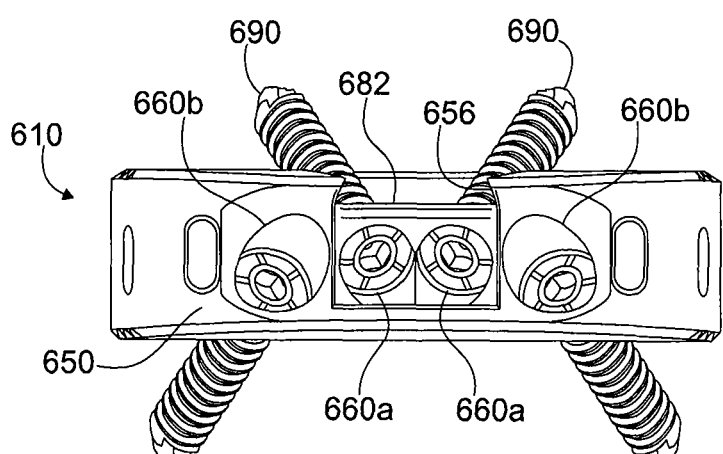
FIG. 15 is a front view of the implant of FIG. 14, showing the implant in a second setting.

Sliding members, such as the inner plates 482, 582 shown in FIGS. 9-13, may be mounted directly into an interbody, rather than a separate outer plate mounted in the body. FIGS. 14-17 show another exemplary implant 610 in accordance with the invention that features direct mounting, and therefore fewer components. Implant 610 has an anterior wall 650 with a pocket 656 that contains an inner plate 682. Inner plate 682 is slidably displaceable within pocket 656 to allow dynamic fixation similar to the implants discussed above. Inner plate 682 includes a pair of inner fastener holes 660a with diverging axes of entry. Anterior wall 650 includes a pair of outer fastener holes 660b also having diverging axes of entry. FIGS. 14 and 15 schematically illustrate the dynamic translation of bone screws 690 during subsidence of implant 610 in one possible scenario. In particular, FIG. 14 illustrates the relative position of bone screws 690 before subsidence of implant 610 into the adjacent end plates. FIG. 15 illustrates the relative position of bone screws 690 after subsidence of implant 610 into the adjacent end plates.

Inner plates may be secured into outer plates or interbodies using a number of connection types. For example, implant 610 uses a sliding pin 686 as seen best in FIGS. 16 and 17. Inner plate 682 includes a central bore 687 that extends through the midsection of the inner plate. Sliding pin 686 extends through bore 687 and supports inner plate 682 at a midsection on the pin. The ends of pin 686 are slidably retained in slots 623 on left and right sides of interbody 620. Slots 623 are elongated in a direction generally perpendicular to the planes of the upper and lower surfaces of body 620. In this arrangement, slots 623 permit a controlled range of movement of inner plate 682 relative to interbody 620 in response to subsidence of implant 610.

Figure 18:
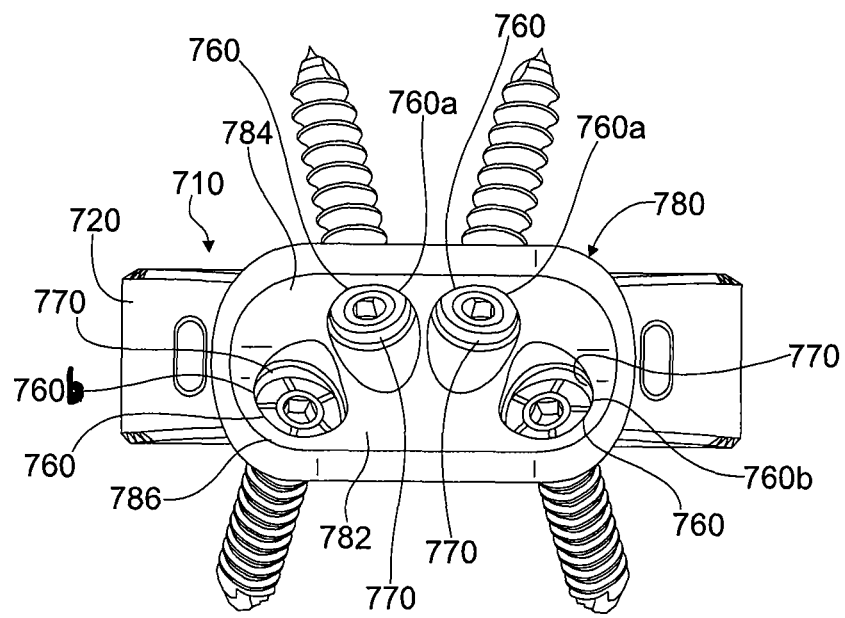
FIG. 18 is a front view of an exemplary implant in accordance with another embodiment of the invention.
Figure 19:
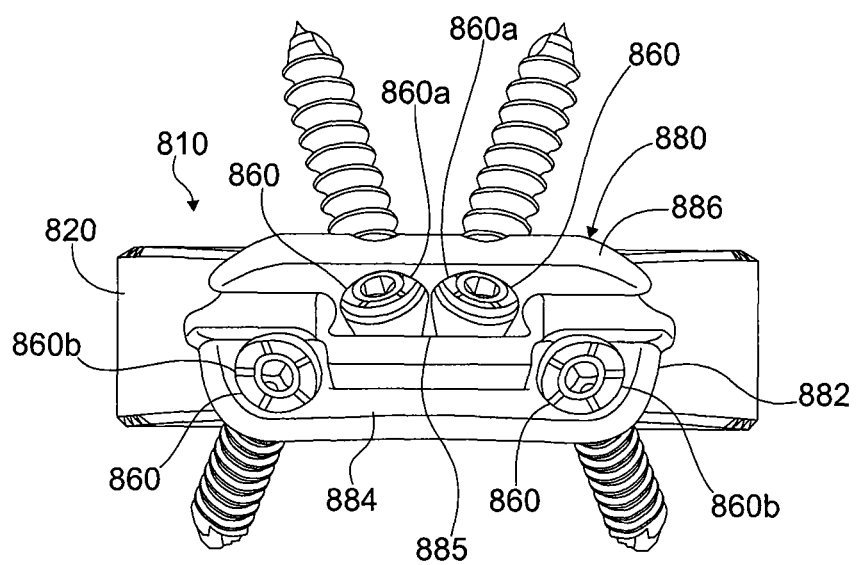
FIG. 19 is a front view of an exemplary implant in accordance with another embodiment of the invention.

The anterior ring apophysis of a vertebral body provides a relatively thick area of cortical bone forming a strong point of fixation for bone screws. Therefore, it may be desirable to adjust the approach angles of bone screws so that the shanks are oriented more directly toward the anterior ring apophysis region. FIGS. 18 and 19 illustrate exemplary implants in accordance with the invention that orient the bone screws so as to penetrate the anterior ring apophysis. FIG. 18 illustrates an implant 710 that includes a body 720 and translation means 780 that includes a fixed ring apophysis plate 782. Ring apophysis plate 782 has a plurality of fastener holes 760 and elongated seats 770 within the fastener holes. Fastener holes 760 have elongated cross sections that allow for translation of bone screws within the holes during subsidence of implant 710. Ring apophysis plate 782 has an upper plate section 784 containing a pair of inner fastener holes 760*a*, and a lower plate section 786 containing a pair of outer fastener holes 760*b*. Upper and lower plate sections 784, 786 extend outwardly from interbody 720 in an anterior direction, and are angled so as to direct the screw shanks into the ring apophysis regions of the superior and inferior vertebrae.

FIG. 19 illustrates an implant 810 that includes a body 820 and translation means 880 that includes a sliding ring apophysis plate 882. Ring apophysis plate 882 has a plurality of fastener holes 860 that are generally cylindrical. Translation of bone screws is facilitated by a pair of sliding plate members that form ring apophysis plate 882. A lower plate member 884 is fixedly mounted to body 820 and contains a pair of outer fastener holes 860. An upper plate member 886 is slidable with respect to the lower plate member 884 through a slot 885 in the lower plate member. The slot 885 in lower plate member 884 is adapted to receive upper plate member 886 during subsidence of implant 810. Upper plate member 886 contains a pair of inner fastener holes 860*a*, and lower plate member 884 contains a pair of outer fastener holes 860*b*. Upper and lower plate members 886, 884 extend outwardly from interbody 820 in an anterior direction, and are angled so as to direct the screw shanks into the anterior ring apophysis regions of the superior and inferior vertebrae.

Figure 20:
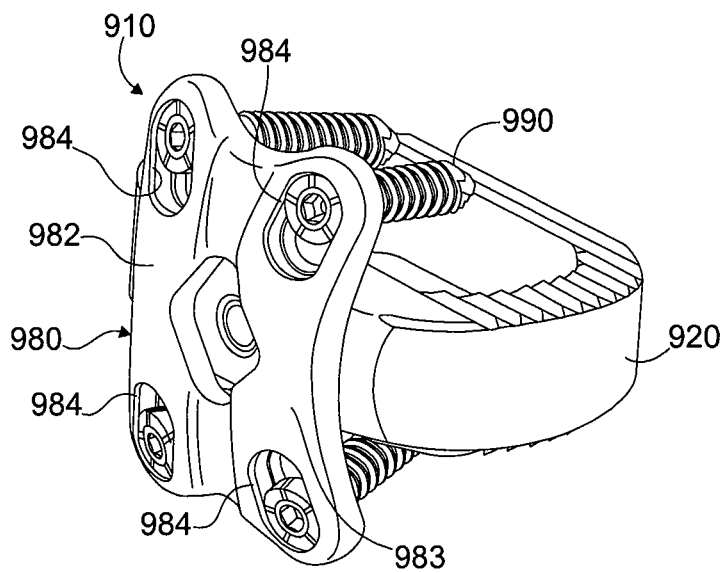
FIG. 20 is a perspective view of an exemplary implant in accordance with another embodiment of the invention.
Figure 21:
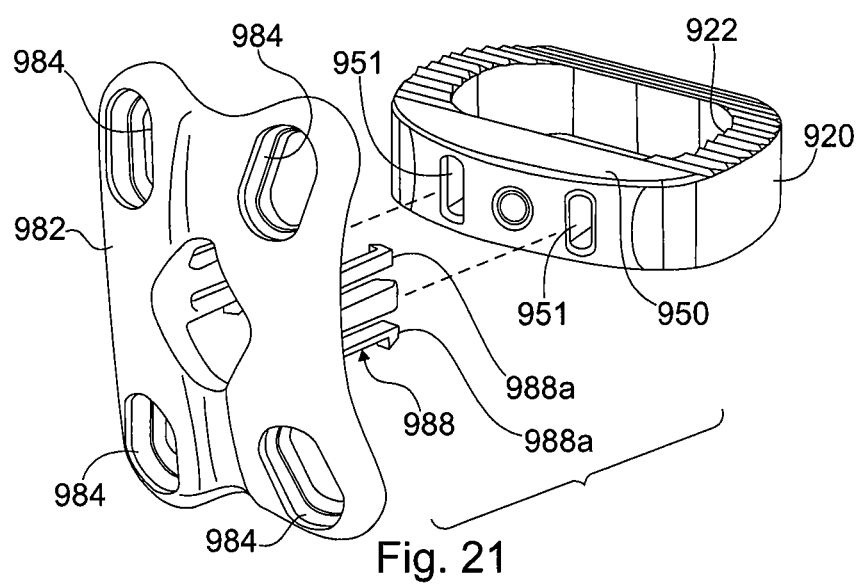
FIG. 21 is an exploded perspective view of components of the implant of FIG. 20.
Figure 22:
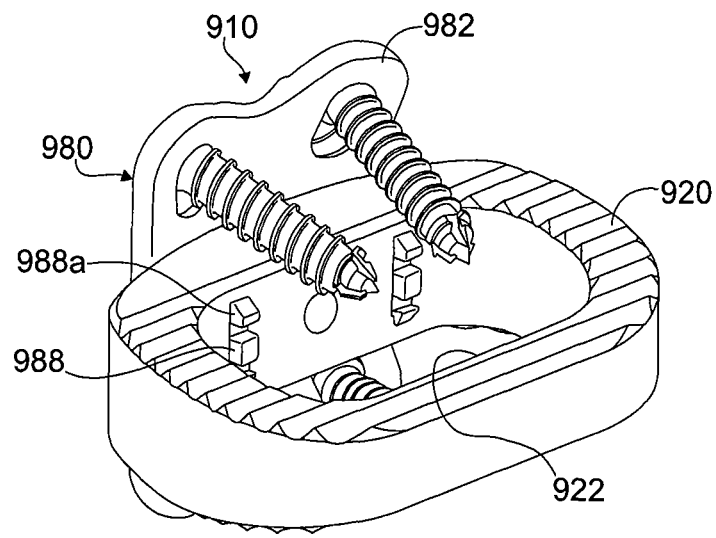
FIG. 22 is another perspective view of the implant of FIG. 20.

Referring to FIGS. 20-22, an exemplary implant 910 in accordance with another embodiment of the invention is shown. Implant 910 features an interbody 920 and a detachable translation mechanism 980. Translation mechanism 980 includes a dynamic fixation plate 982 with slotted openings 984. A plurality of bone screws 990 extend through slotted openings 984. Fixation plate 982 includes a rigid body 983 that reinforces the fusion site, while allowing for controlled translation of bone screws during subsidence. The anterior face of fixation plate 982 is substantially smooth with rounded edges to minimize damage to blood vessels and other neighboring structures. The rear or posterior-facing side of fixation plate 982 includes a pair of tab connectors 988. Each tab connector 988 has a pair of opposing catch tabs 988*a* that detachably engage an anterior side 950 of interbody 920. Anterior side 950 includes a pair of slots 951 adapted to receive tab connectors 988. Catch tabs 988*a* are configured to flex inwardly during entry into and passage through slots 951, and then snap outwardly after exiting the slots into the hollow interior 922 of body 920. Catch tabs 988*a* rest against the inner wall surrounding the hollow interior 922 to prevent reversing the tab connectors 988 out of slots 951, as shown in FIG. 22.

Figure 23:
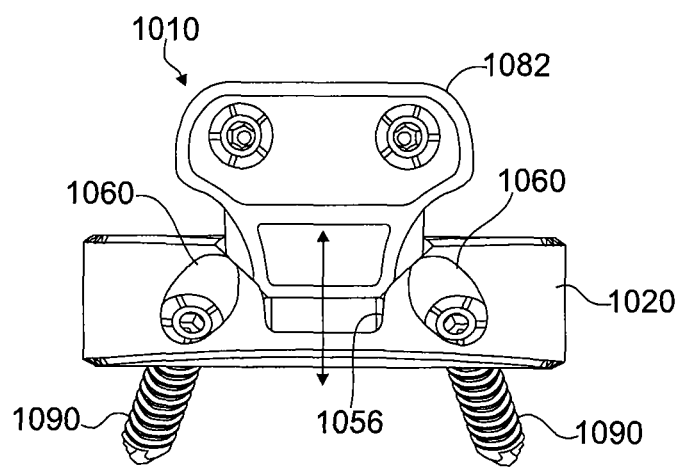
FIG. 23 is a front view of an exemplary implant in accordance with another embodiment of the invention.

Referring now to FIG. 23, an exemplary implant 1010 in accordance with another embodiment of the invention is shown, which features an interbody 1020 and a translation mechanism in the form of a dynamic buttress plate 1082. Buttress plate 1082 is slidably received in an anterior slot 1056 on interbody 1020 to adjust for subsidence of the implant 1010. A pair of screws 1090 are inserted through fastener holes 1060 as shown to attach buttress plate 1082 to a vertebral body. Once buttress plate 1082 is secured to the vertebral body, the buttress plate slides in the direction shown by the arrows.

As noted above, the anterior surface of the implant may lie in proximity to blood vessels that can be injured by sharp edges or projections on the implant. Where this is a risk, embodiments of the invention may include smooth contours on their anterior surfaces, such as rounded corners and recessed fastener holes, to minimize the potential for injury to surrounding blood vessels, soft tissue and other structures during subsidence and movement of the implant and its components. Smooth contours may be used on the anterior surface of the interbody, or on a separate component placed over the anterior surface of the interbody. For example, the anterior surface of the interbody may be partially enclosed inside a cover or shield.

Figure 24:
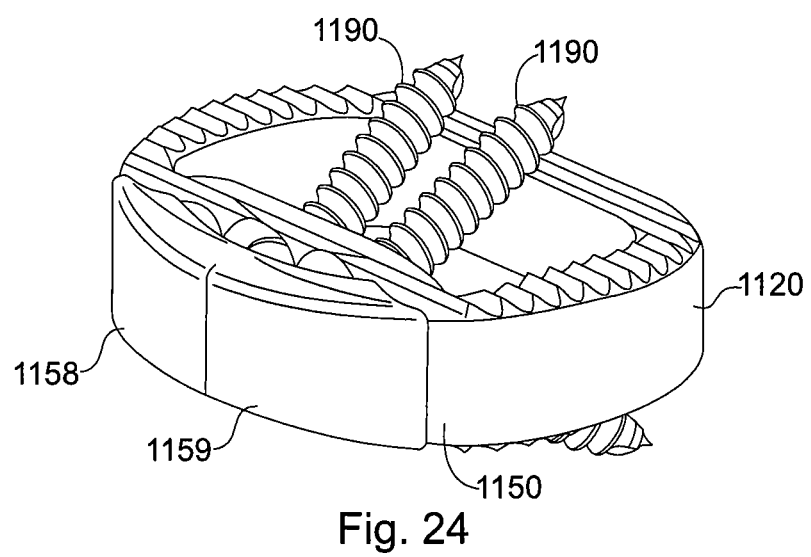
FIG. 24 is a perspective view of an exemplary implant in accordance with another embodiment of the invention.

Referring to FIG. 24, an exemplary cover 1158 is shown on an interbody 1120. Cover 1158 extends over an anterior surface 1150 of interbody 1120 to enclose the heads of fasteners 1190 inserted into the interbody. A smooth rounded exterior surface 1159 on cover 1158 forms a continuous rounded perimeter with the sidewalls of interbody 1120. Rounded surface 1159 may contact and slide against blood vessels, tissue and other sensitive structures without damaging them. Cover 1158 extends over fasteners 1190 without contacting or interfering with the fastener heads in the slotted openings 1160. Interbody 1120 and cover 1158 may include cooperating tabs and slots, or other types of connectors to facilitate attachment of the two components.

A cover such as cover 1158 provides several advantages. For example, as noted above, a cover can provide a relatively smooth surface that contacts and slides against blood vessels without damaging them. As a related benefit, a cover provides a protective barrier that substantially prevents back out of screws into blood vessels or other nearby structures. A cover further provides additional mass on the anterior portion of interbody 1120, increasing the strength of the anterior load column of the vertebral body. Moreover, a cover can provide an active surface that promotes attachment to adjacent tissue cells. The cover may include a bioactive coating, for example, that promotes or controls adhesion of tissue cells. Tissue cells that attach to the cover may further stabilize the implant and provide a source for secondary fixation that is not influenced by subsidence or relative movement of the fasteners in the interbody, which are separated from the tissue by the cover.

While preferred embodiments of the invention have been shown and described herein, it will be understood that such embodiments are provided by way of example only. Numerous variations, changes and substitutions will occur to those skilled in the art without departing from the spirit of the invention. For example, the interbodies, plates and other components that are illustrated herein with round fastener holes may alternatively feature slotted fastener holes to alter the dynamic characteristics of those components and their respective implants. Accordingly, it is intended that the appended claims cover all such variations as fall within the scope of the invention.

What is claimed:
1. An intervertebral implant comprising:
a rigid ring-shaped body with a hollow interior, the hollow interior forming a bone graft space;
an upper surface on the body generally conforming to a plane;
a lower surface on the body generally conforming to a plane;
a fastener hole extending transversely through the ring-shaped body and the fastener hole having a longitudinal axis extending transversely through at least one of the planes of the upper surface and the lower surface; and
means for translating a fastener seated within the fastener hole with respect to the implant, the means comprising a lower plate member and an upper plate member that is slidably displaceable with respect to the lower plate member.

2. The intervertebral implant of claim 1 wherein the fastener hole passes through the upper plate member.

3. The intervertebral implant of claim 1 wherein the fastener hole comprises a first fastener hole having a longitudinal axis extending transversely through the plane of the upper surface, the implant further comprising a second fastener hole having a longitudinal axis extending transversely through the plane of the lower surface.

4. The intervertebral implant of claim 3 further comprising a third fastener hole having a longitudinal axis extending transversely through the plane of the upper surface, and a fourth fastener hole having a longitudinal axis extending transversely through the plane of the lower surface.

5. An intervertebral implant comprising:
a rigid ring-shaped body with a hollow interior, the hollow interior forming a bone graft space;
an upper surface on the body generally conforming to a plane;
a lower surface on the body generally conforming to a plane;
a slot extending transversely through the ring-shaped body and the slot having a longitudinal axis extending transversely through at least one of the planes of the upper surface and the lower surface;
a lower plate member fixedly mounted to the body; and
an upper plate member slidable with respect to the lower plate member.

6. The intervertebral implant of claim 5, wherein the implant comprises an anterior face, and the slot extends through the anterior face, the slot comprising a seat recessed in the anterior face.

7. An intervertebral implant comprising:
a rigid ring-shaped body with a hollow interior, the hollow interior forming a bone graft space;
an upper surface on the body for at least partial engagement with an end plate of a first vertebrae, the upper surface generally conforming to a plane;
a lower surface on the body for at least partial engagement with an end plate of a second vertebrae, the lower surface generally conforming to a plane;
a first fastener hole extending transversely through the rigid ring-shaped body and having a longitudinal axis extending transversely through the plane of the upper surface;
a second fastener hole having a longitudinal axis extending transversely through the plane of the lower surface;
a lower plate member; and
an upper plate member slidably displaceable with respect to the lower plate member.

8. The intervertebral implant of claim 7, wherein the implant comprises an anterior face, the first and second fastener holes extending through the anterior face.

9. The intervertebral implant of claim 8, wherein the anterior face is formed on the upper plate member and lower plate member.

10. An intervertebral implant comprising:
a rigid ring-shaped body with a hollow interior, the hollow interior forming a bone graft space;
an upper surface and a lower surface;
a lower plate member;
an upper plate member slidably displaceable with respect to the lower plate member in a plane passing through the upper surface and the lower surface; and
a fastener slot extending through the upper plate, the fastener slot having a longitudinal axis extending transversely through the rigid ring-shaped body and transversely through the upper surface.

11. The intervertebral implant of claim 10, wherein the lower plate member forms a slot, the upper plate member being slidably displaceable in the slot.

12. The intervertebral implant of claim 10, wherein the fastener slot comprises a first slot, the implant further comprising a second slot, the first and second slots both passing through the upper plate member.

13. The intervertebral implant of claim 10, wherein the upper surface and the lower surface are formed on the body, and wherein the upper plate member and lower plate member extend outwardly from the body in an anterior direction.

14. An intervertebral implant comprising:
a rigid ring-shaped body with a hollow interior, the hollow interior forming a bone graft space;
an upper surface on the body for at least partial engagement with an end plate of a first vertebrae;
a lower surface on the body for at least partial engagement with an end plate of a second vertebrae;
an anterior surface extending between the upper surface and the lower surface;
a ring apophysis plate attached to the anterior surface, the ring apophysis plate comprising a lower plate member fixedly mounted to the anterior surface and an upper plate member slidable with respect to the lower plate member, and
a fastener hole extending through the upper plate member, the fastener hole extending transversely through the rigid ring-shaped body and the fastener hole having a longitudinal axis extending transversely through the upper surface.

15. The intervertebral implant of claim 14, wherein the lower plate member comprises a slot adapted to receive the upper plate member during subsidence of the implant.

16. The intervertebral implant of claim 14, wherein the fastener hole extending through the upper plate member comprises a pair of inner fastener holes.

17. The intervertebral implant of claim 14, wherein the ring apophysis plate comprises a plurality of fastener holes and a plurality of screw fasteners extending through the fastener holes.

* * * * *